United States Patent
Liu et al.

(10) Patent No.: US 6,719,999 B2
(45) Date of Patent: *Apr. 13, 2004

(54) FORMULATIONS COMPRISING LIPID-REGULATING AGENTS

(75) Inventors: Rong (Ron) Liu, Gurnee, IL (US); Qinghai Pan, Lake Bluff, IL (US); Pawan Hansrani, Buffalo Grove, IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 28 days.

(21) Appl. No.: 09/283,083

(22) Filed: Mar. 31, 1999

(65) Prior Publication Data

US 2001/0006658 A1 Jul. 5, 2001

(51) Int. Cl.$^7$ .................................................. A61K 9/48
(52) U.S. Cl. ........................ 424/451; 424/455; 424/456; 424/400
(58) Field of Search .................. 514/506, 45, 463, 514/489, 451; 424/400, 455, 456

(56) References Cited

U.S. PATENT DOCUMENTS

| 4,058,552 A | 11/1977 | Mieville |
| 4,739,101 A | 4/1988 | Bourgogne et al. |
| 4,800,079 A | 1/1989 | Boyer |
| 4,859,703 A * | 8/1989 | Krause .................... 514/543 |
| 4,895,726 A | 1/1990 | Curtet et al. |
| 4,925,676 A | 5/1990 | Ghebre-Sellassie et al. |
| 4,927,639 A | 5/1990 | Ghebre-Sellassie et al. |
| 4,957,746 A | 9/1990 | Valducci |
| 4,961,890 A | 10/1990 | Boyer |
| 5,030,447 A | 7/1991 | Joshi et al. |
| 5,180,589 A | 1/1993 | Joshi et al. |
| 5,545,628 A | 8/1996 | Deboeck et al. |
| 5,645,856 A | 7/1997 | Lacy et al. |
| 5,691,375 A * | 11/1997 | Behounek et al. .......... 514/510 |
| 5,776,495 A * | 7/1998 | Duclos et al. .............. 424/455 |
| 5,827,536 A * | 10/1998 | Laruelle .................... 424/451 |
| 6,027,747 A * | 2/2000 | Terracol et al. ............. 424/455 |
| 6,287,594 B1 * | 9/2001 | Wilson et al. .............. 424/451 |

FOREIGN PATENT DOCUMENTS

| EP | 0793958 | 9/1997 |
| WO | WO 8201649 | 5/1982 |
| WO | WO 92/10996 | 7/1992 |
| WO | WO 95/24893 | 9/1995 |
| WO | WO 96/36318 | 11/1996 |

OTHER PUBLICATIONS

Physicians' Desk Reference, 52 Edition, pp. 808&2103 (Medical Economics Company, Inc., NJ, 1998).*
Ming–Thau Sheu et al., Characterization and Dissolution of Fenofibrate Solid Dispersion Systems, *International Journal of Pharmaceutics*, (1994), p. 137–146.
G. F. Palmieri et al., Characterization and Dissolution Studies of PEG 4000/Fenofibrate Solid Dispersions, *S.T.P. Pharma Sciences*, (1996), pp. 188–194.

* cited by examiner

*Primary Examiner*—Thurman K. Page
*Assistant Examiner*—Robert M. Joynes
(74) *Attorney, Agent, or Firm*—Wood, Phillips, Katz, Clark & Mortimer

(57) ABSTRACT

The present invention is directed to a formulation comprising a lipid-regulating agent dissolved in one or more non-aqueous and/or water-miscible solvents, or optionally, in a premix of one or more solvents and one or more surfactants.

10 Claims, 1 Drawing Sheet

FORMULATIONS COMPRISING LIPID-REGULATING AGENTS

FIELD OF THE INVENTION

The present invention relates to novel formulations comprising lipid-regulating agents.

BACKGROUND OF THE INVENTION

2-[4-(4-chlorobenzoyl)phenoxy]-2-methyl-propanoic acid, 1-methylethylester, also known as fenofibrate, is representative of a broad class of compounds having pharmaceutical utility as lipid regulating agents. More specifically, this compound is part of a lipid-regulating agent class of compounds commonly known as fibrates, and is disclosed in U.S. Pat. No. 4,058,552.

Fenofibrate has been prepared in several different formulations, c.f., U.S. Pat. No. 4,800,079 and U.S. Pat. No. 4,895,726. U.S. Pat. No. 4,895,726 discloses a co-micronized formulation of fenofibrate and a solid surfactant.

U.S. Pat. No. 4,961,890 discloses a process for preparing a controlled release formulation containing fenofibrate in an intermediate layer in the form of crystalline microparticles included within pores of an inert matrix. The formulation is prepared by a process involving the sequential steps of dampening said inert core with a solution based on said binder, then projecting said fenofibrate microparticles in a single layer onto said dampened core, and thereafter drying, before said solution based on said binder dissolves said fenofibrate microparticles, and repeating said three steps in sequence until said intermediate layer is formed.

European Patent Application No. EP0793958A2 discloses a process for producing a fenofibrate solid dosage form utilizing fenofibrate, a surface active agent and polyvinyl pyrrolidone in which the fenofibrate particles are mixed with a polyvinyl pyrrolidone solution. The thus obtained mixture is granulated with an aqueous solution of one or more surface active agents, and the granulate thus produced is dried.

PCT Publication No. WO 82/01649 discloses a fenofibrate formulation having granules that are comprised of a neutral core that is a mixture of saccharose and starch. The neutral core is covered with a first layer of fenofibrate, admixed with an excipient and with a second microporous outer layer of an edible polymer.

U.S. Pat. No. 5,645,856 describes the use of a carrier for hydrophobic drugs, including fenofibrate, and pharmaceutical compositions based thereon. The carrier comprises a digestible oil and a pharmaceutically-acceptable surfactant component for dispersing the oil in vivo upon administration of the carrier, which comprises a hydrophilic surfactant, said surfactant component being such as not to substantially inhibit the in vivo lipolysis of the digestible oil.

Gemfibrozil is another member of the fibrate class of lipid-regulating agents. U.S. Pat. No. 4,927,639 discloses a disintegratable formulation of gemfibrozil providing both immediate and sustained release, comprising a tablet compressed from a mixture of a first and second granulation, and a disintegration excipient operable to effect partial or complete disintegration in the stomach. The first granulation comprises finely divided particles of pure gemfibrozil granulated with at least one cellulose derivative, and the second granulation comprises finely divided particles of pure gemfibrozil granulated with a pharmaceuitcally-acceptable water soluble or insoluble polymer which are then uniformly coated with a pharmaceutically-acceptable (meth)acylate copolymer prior to admixture with the first granulation. The first and second granulations are present in the final composition in a ratio of from about 10:1 to about 1:10.

U.S. Pat. No. 4,925,676 discloses a disintegratable gemfibrozil tablet providing both immediate and enteric release, which is compressed from a mixture of a first granulation of gemfibrozil with at least one acid-disintegratable binder, and a second granulation formed from the first granulation, but regranulated or coated with an alkali-disintegratable formulation of at least one substantially alkali-soluble and substantially acid-insoluble polymer.

Another class of lipid-regulating agents are commonly known as statins, of which pravastatin and atorvastatin are members. U.S. Pat. Nos. 5,030,447 and 5,180,589 describe stable pharmaceutical compositions, which when dispersed in water have a pH of at least 9, and include a medicament which is sensitive to a low pH environment, such as prevastatin, one or more fillers such as lactose and/or microcrystalline cellulose, one or more binders, such as microcrystalline cellulose (dry binder) or polyvinylpyrrolidone (wet binder), one or more disintegrating agents such as croscarmellose sodium, one or more lubricants such as magnesium stearate and one or more basifying agents such as magnesium oxide.

It is an object of the present invention to provide formulations of lipid-regulating agents having enhanced bioavailability when compared to commercially available formulations.

SUMMARY OF THE INVENTION

The present invention is directed to a formulation comprising a lipid-regulating agent dissolved in one or more non-aqueous and/or water-miscible solvents to form a concentrate. The formulation forms a lipid-regulating agent-containing composition when mixed with water or any aqueous solutions. Preferably, the formulation further comprises one or more water-miscible surfactants which is(are) mixed with said solvent(s). The composition results in an increase in drug solubility and oral bioavailability.

The formulation may be administered directly, diluted into an appropriate vehicle for administration, encapsulated into soft or hard gelatin capsules for administration, or administered by other means obvious to those skilled in the art.

DETAILED DESCRIPTION OF THE INVENTION

Figure 1:
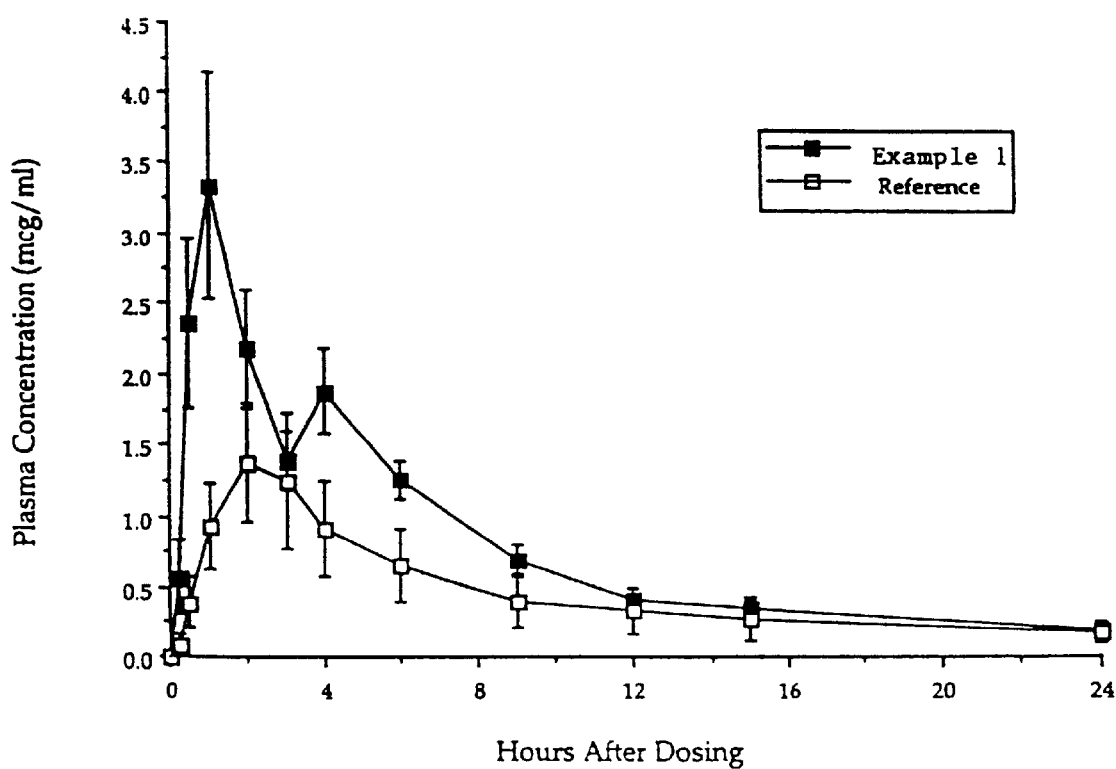
FIG. 1 is a graph showing the plasma concentration in fasted dogs of the formulation of Example 1 and a reference compound.

The bulk lipid-regulating agent may be prepared by any available method, as for example the compound fenofibrate may be prepared by the procedure disclosed in U.S. Pat. No. 4,058,552, or the procedure disclosed in U.S. Pat. No. 4,739,101, both herein incorporated by reference.

The formulation comprising the lipid-regulating agent is prepared by mixing one or more solvents, and optionally one or more surfactants, then adding the lipid-regulating agent and mixing well until dissolved.

The delivery system of the present invention results in increased solubility, half-life and bioavailability of the lipid-regulating agent. It can be further diluted with additional liquids or it may be thickened and/or stabilized with various pharmaceutical excipients to vary its existing properties Suitable solvents include any pharmaceutically acceptable non-aqueous or water-miscible solvent, such as, for example, ethyl alcohol, isopropanol alcohol, glycerine, propylene glycol, polyethylene glycol, Arlasolve DMI (dimethyl isosorbide; ICI).

Suitable surfactants include any surfactant in which fenofibrate is highly soluble. Such surfactants will typically be those with HLB values ranging from about 1 to about 20. Representative surfactants include Labrafac Lipophile WL 1349 (triglyceride of caprylic/capric acid; Gattefosse), Lauroglycol FCC (propylene glycol laurate; Gattefosse), Labrafil M 1944 CS (glyceryl and polyethylene glycol esters; Gattefosse), Span 80 (sorbitan monooleate; Sigma), Capmul MCM (mono/diglycerides of caprylic/capric acid in glycerol; Abitec), Arlacel 83 (sorbitan sesquioleate; ICI), Brij 93 (polyoxyethylene (2) oleyl ether; READ ICI), Acconon E (polyoxypropylene 15 stearyl ether; Abitec), Labrafil M 2125 CS (unsaturated polyglycolyzed glycerides; Gattefose), Maisine 35-1 (glyceryl monolinoleate; Gattefosse), Sorbitan Oleate NF (Crill #4; Croda), Caprol 10G100 (decaglyceryl decaoleate; Abitec), Labrafil Isostearique (triisostearin PEG 6 esters; Gattefosse), Caprol 3G0 triglyceryl monoleate; Abitec), Peceol (glyceryl monooleate; Gattefosse), G-950 (sorbide dioleate; ICI), Arlacel 989 (polyoxyethylene castor wax; ICI), Labrafac CM 10 (polyglycolysed glycerides; Gattefosse), Labrafac CM 12 (polyglycolysed glycerides; Gattefosse), Labrasol (saturated C8-C10 polyglycolysed glycerides; Gattefosse), Tween 80 (polyoxyethylene (20) sorbitan monooleate; Sigma), Tween 85 (polyoxyethylene (20) sorbitan trioleate; Sigma), Pluronic L43 (copolymers of propylene oxide and ethylene oxide; BASF), Pluronic 17R4 (copolymers of propylene oxide and ethylene oxide; BASF), Cremophor EL (polyoxyl 35 castor oil; BASF), Accomid PK (palm kernelamide DEA; Abitec), Brij 30 (polyoxyethylene 4 lauryl ether; READ ICI), Arlasolve 200 liquid (polyoxyethylene (20) isohexadecyl ether; ICI), Arlacel 20 (sorbitan monolaurate; ICI), Renex 38 (alcohol ethoxylate; ICI), G-4280 (polyoxyethylene 80 sorbitan monolaurate; ICI), Caprol 6G20 (hexaglyceryl dioleate; Abitec), Crillet 4 Ultra (polysorbate 80; Croda), Crodesta SL-40 (sucrose laurate; Croda), Cirrasol G-265 (quaternary ammoniun salt; ICI), Cirrasol G-1096 (polyoxyethylene sorbitol hexaoleate; ICI), Softigen 767 (caprylic/capric acid partial glyceride-6 EO; HULS America), Witconol 14 (polyglyceryl 4 oleate; Witco).

Preferred surfactants include Labrafac Lipophile WL 1349 (triglyceride of caprylic/capric acid; Gattefosse), Labrofac CM 10 and CM 12 (polyglycolysed glycerides; Gattefosse), Lauroglycol FCC (propylene glycol laurate; Gattefosse), Peceol (glyceryl monooleate; Gattefosse), Caprol 3G0 (triglyceryl monoleate; Abitec), Capmul MCM (mono/diglycerides of caprylic/capric acid in glycerol; Abitec), Labrasol (saturated C8-C10 polyglycolysed glycerides; Gattefosse), Tween 80 (polyoxyethylene (20) sorbitan monooleate; Sigma), Pluronic L43 (copolymers of propylene oxide; BASF), Pluronic 17R4 (copolymers of propylene oxide and ethylene oxide; BASF), Cremophor EL (polyoxyl 35 castor oil; BASF), Brij 30 (polyoxyethylene 4 lauryl ether; READ ICI), Arlacel 20 (sorbitan monolaurate; ICI), Renex 38 (alcohol ethoxylate; ICI).

Suitable oils include, but are not limited to, any pharmaceutically acceptable oil, such as, for example, Labrafac Lipophile WL 1349 (triglyceride of caprylic/capric acid; Gattefosse), Myvacet 9-08 (distillated acetylated monoglycerides: ), Myvacet 9-40 (distillated acetylated monoglycerides: ), Capmul PG-8 (propylene glycol and mono/dicaprylate; Abitec), Arlamol E (polyoxypropylene (15) stearyl alcohol; ICI), Captex 300 (glyceryl tricaprylate/caprate; Abitec), olive oil, Miglyol 812 (caprylic/capric triglycerides; HULS America), sesame oil (Sigma), Novol (oleyl alcohol, Croda). Preferred oils include Labrafac Lipophile WL 1349, Myvacet 9-08, Myvacet 9-40, and Capmul PG-8

Other optional ingredients which may be included in the compositions of the present invention are those which are conventionally used in oil-based drug delivery systems, e.g. antioxidants such as, for example, tocopherol, ascorbyl palmitate, ascorbic acid, butylated hydroxytoluene, butylated hydroxyanisole, propyl gallate, etc.; pH stabilizers such as, for example, citric acid, tartaric acid, fumaric acid, acetic acid, glycine, arginine, lysine, potassium hydrogen phosphate, etc.; thickeners/suspending agents such as, for example, hydrogenated vegetable oils, beeswax, colloidal silicon dioxide, gums, celluloses, silicates, bentonite, etc.; flavoring agents such as, for example, cherry, lemon, aniseed flavors, etc.; sweeteners such as, for example, aspartame, saccharin, cyclamates, etc.; adsorbents such as, for example, lactose, sorbitol, high molecular weight polyethylene glycols, such as, for example, PEG 1475, PEG 8000, etc., and hydrophilic polymers, such as, for example, Avicel PH 101 (microcrystalline cellulose; FMC), hydroxypropylmethyl cellulose, etc.

The resulting liquid comprising the lipid-regulating agent may be dosed directly for oral administration, diluted into an appropriate vehicle for oral administration, filled into soft or hard capsules for oral administration, or delivered by some other means obvious to those skilled in the art. The said liquid can be used to improve the oral bioavailability, and increase the solubility of said lipid-regulating agent.

The invention will be understood more clearly from the following non-limiting representative examples:

EXAMPLE 1

Fenofibrate (6.7 gm) was mixed with dimethyl isosorbide (25 gm) until dissolved. Labrafac Lipophile WL 1349 (Gattefosse) (25 gm) was added to the solution. Mixing was continued until a clear solution is obtained. 0.567 gm of the final solution (containing 67 mg fenofibrate) was filled into hard gelatin capsules.

EXAMPLE 2

Pravastatin (5.0 g) is mixed with dimethyl isosorbide (25 g) until dissolved. Labrafac Lipophile WL 1349 (25 g) is added to the solution. Mixing is continued until a clear solution is obtained. Appropriate amount of solution may be filled into capsules to provide the desired dose.

EXAMPLE 3

Capsules prepared by the process described in Example 1, and from a commercial fenofibrate composition, Lipanthyl 67M (Groupe Fournier) (Reference), were administered to a group of dogs at a dose of 67 mg fenofibrate/dog (10 mL emulsion or one capsule/dog). The plasma concentrations of fenofibric acid were determined by HPLC. Concentrations were normalized to a 6.7 mg/kg dose in each dog. FIG. 1 presents the resulting data in graph form. The results provided as mean±SD, n=6, were as follows:

Lipanthyl 67M (Reference):
Cmax=1.88±0.97 mcg/ml
Tmax=1.6±0.9 hr
t½=4.5 hr
AUC (0–24)=11.08±9.42 mcg·hr/ml
Capsules of Example 1:
Cmax=5.35±2.35 mcg/ml
Tmax=1.5±0.8 hr
t½=5.6 hr
AUC (0–24)=26.16±6.43 mcg·hr/ml
AUC relative to Reference=3.0

What is claimed is:

1. A composition comprising a fibrate dissolved in one or more water miscible solvents selected from the group consisting of glycerin and propylene glycol.

2. A composition of claim 1 further comprising a fibrate dissolved in a mixture of one or more solvents and optionally, one or more surfactants.

3. A composition of claim 1 wherein said fibrate is fenofibrate.

4. A composition of claim 2 wherein at least one or more of said surfactants is selected from propylene glycol laurate, glyceryl and polyethylene glycol esters, sorbitan monooleate, mono/diglycerides of caprylic/capric acid, sorbitan sesquioleate, polyoxyethylene ether, polyoxypropylene 15 stearyl ether, unsaturated polyglycolyzed glycerides, glyceryl monolinoleate, decaglyceryl decaoleate, triisostearin polyethylene glycol 6 esters, triglyceryl monoleate, glyceryl monooleate, sorbide dioleate, polyoxyethylene, castor wax, polyoxyethylene (20) sorbitan monooleate, polyoxyethylene (20) sorbitan trioleate, copolymers of propylene oxide and ethylene oxide, polyoxyl (35) castor oil, palm kernelamide DEA, polyoxyethylene (4) lauryl ether, polyoxyethylene (20) isohexadecyl ether, sorbitan monolaurate, alcohol ethoxylate, polyoxyethylene (80) sorbitan monolaurate, hexaglyceryl dioleate, polysorbate (80), sucrose laurate, quaternary ammoniun salt, polyoxyethylene sorbitol hexaoleate, caprylic/capric acid partial glyceride-6 ethylene oxide, polyglyceryl (4) oleate.

5. A composition of claim 4 wherein at least one or more of said surfactants is triglyceride of caprylic/capric acid, polyglycolysed glycerides, propylene glycol laurate, glyceryl monooleate, triglyceryl monoleate, mono/diglycerides of caprylic/capric acid in glycerol, saturated C8–C10 polyglycolysed glycerides, polyoxyethylene (20) sorbitan monooleate, copolymers of propylene oxide, copolymers of propylene oxide and ethylene oxide, polyoxyl 35 castor oil, polyoxyethylene 4 lauryl ether, sorbitan monolaurate, alcohol ethoxylate.

6. A delivery system comprising a composition of claim 1.

7. A delivery system of claim 6 wherein said delivery system is a capsule.

8. A method of treating hyperlipidemia comprising the administration of a composition of claim 1 to a patient.

9. A method of treating hyperlipidemia comprising the administration of a composition of claim 3 to a patient.

10. A method of treating hyperlipidemia comprising the administration of a composition of claim 7 to a patient.

* * * * *